United States Patent

Kekez

[19]

[11] Patent Number: 5,882,591
[45] Date of Patent: Mar. 16, 1999

[54] METHOD AND APPARATUS FOR DISINFECTING BIOLOGICAL FLUIDS THROUGH INTERACTION WITH GASES

[76] Inventor: Mladen M. Kekez, 2104 Alta Vista Drive, Ottawa, Ontario, Canada, K1H 7L8

[21] Appl. No.: 906,965

[22] Filed: Aug. 6, 1997

[30] Foreign Application Priority Data

Feb. 7, 1995 [GB] United Kingdom .................... 9502347

[51] Int. Cl.$^6$ ........................................................ A61L 2/08
[52] U.S. Cl. .............................. 422/28; 422/22; 422/33; 422/305; 422/306; 239/3
[58] Field of Search ................................. 422/22, 24, 28, 422/33, 305, 306; 239/3

[56] References Cited

U.S. PATENT DOCUMENTS

| | | | |
|---|---|---|---|
| 3,977,568 | 8/1976 | Smith ........................................ | 222/80 |
| 4,019,983 | 4/1977 | Mandt ....................................... | 210/754 |
| 4,632,980 | 12/1986 | Zee et al. ................................. | 530/380 |
| 5,173,274 | 12/1992 | Owen ....................................... | 422/306 |
| 5,482,828 | 1/1996 | Lin et al. ................................... | 435/2 |

Primary Examiner—Robert Warden
Assistant Examiner—Fariborz Moazzam
Attorney, Agent, or Firm—Juliusz Szereszewski

[57] ABSTRACT

Biological fluids, e.g. bodily fluids such as plasma/serum, semen, milk or blood, can be treated efficiently with ozone to inactivate certain viruses, bacteria, fungi etc. To effect and enhance the contact of such fluids with ozone, or another disinfecting or deactivating gas, the fluids are thoroughly nebulized, or atomized, i.e. dispersed into minute droplets. Nebulization has been found to afford a faster $O_3$-fluid reaction rate than other known methods. It is proposed to create a fine "rain" of droplets to fall through a controlled atmosphere of $O_3/O_2$ and/or $O_3$/inert gas mixture. Electric and magnetic fields are superimposed over the space through which the droplets are passed.

Three types of nebulizers/atomizers are described: compressed gas ($O_3/O_2$ mixture) atomizer, ultrasonic nebulizer, and rotary nebulizer.

The invention was tested on coliphage MS2 which is safe, easy to handle, and more resistant to chemical disinfections than viruses such as HIV. More than 7 $\log_{10}$ reduction in the virus viability was observed.

20 Claims, 7 Drawing Sheets

METHOD AND APPARATUS FOR DISINFECTING BIOLOGICAL FLUIDS THROUGH INTERACTION WITH GASES

FIELD OF THE INVENTION

This invention relates to disinfecting biological fluids and particularly bodily liquids such as blood, plasma, serum or milk which may contain pathogenic agents, by contacting such fluids with a gas containing a proper deactivating component.

BACKGROUND ART

For the past three decades, ozone has been of value in the treatment of viral infections and pathogenic microorganisms. In this respect, the following references can be related to: Australian patent application No. 9056278 dated Dec. 05, 1991; Zee et al. U.S. Pat. No. 4,632,980 dated Jun. 26, 1990; EP patent application No. 86071 dated Aug. 17, 1983; German Patent No. 1068428 dated May 21, 1957; D. C. Bolton. et al, The biological effects of ozone on representative members of five groups of animal viruses, Environmental Research, 27, 1982, pp 476–484; Wells et al, Inactivation of human immunodeficiency virus type 1 by ozone in vitro, Blood, 78, 1991, pp. 1882–1890; Garber et al, The use of ozone-treated blood in the therapy of HIV infection and immune disease: a pilot study of safety and efficacy, AIDS, 5, 1991 pp.981–984; M. T. F. Carpendale and J. K. Freeberg, Ozone inactivates HIV at noncytotoxic concentrations, Antiviral Research, 16, 1991, 281–292; C. E. Cross et al, Oxidative damage to plasma constituents by ozone, FEBS Letters, 298, 1992, pp 269–272; J. M. Vaughn et al, Inactivation of human and simian rotaviruses by ozone, 53, 1987, pp. 2218–2221; S. D. Razumovskii and G. E. Zaikov, Ozone and its reaction with organic compounds, 1984, Amsterdam: Elsevier; K. Rietema and C. G. Verver, Cyclones in industry, 1961, Amsterdam: Elsevier.

It has been suggested that ozone could inactivate most infectious viruses without altering the physiological and antigenic properties of body fluids. Ozone should not cause substantial cytotoxicity to lymphocytes or decrease the levels of factor VIII in anti-haemophiliac factor.

Two prior art methods, viz. the bubbling method, known as Müller method (German Patent 1068428) and the "hollow fibre" method of Wells et al. (also AU patent application 9056278) do not ensure consistent ozone transfer to the body fluids thus treated. The method of Bolton et al. (U.S. Pat. No. 4,632,980) where the reaction of ozone with the virus suspensions is carried out in a thin film on the surface of a rotating bottle, produces consistent results but it is time demanding.

The original Müller system suggests a technique by which 10 mL of blood is removed from a patient by phlebotomy, exposed for 3 to 30 min to ozone and immediately re-injected intramuscularly into the patient. Such output is hardly satisfactory for commercial purposes.

It is desirable to develop a process and apparatus for consistently deactivating deleterious substances and factors such as viruses and microorganisms contained in biological fluids, e.g. bodily fluids, by contacting such fluids with certain deactivating gases, e.g. ozone, the process having relatively high reliability and efficacy. Relatively simple, low cost means of inactivating e.g. viruses in body fluids are likely to be in demand in blood transfusion centres, hospitals, and veterinary practices.

DISCLOSURE OF THE INVENTION

According to the invention, there is provided a method of disinfecting biological fluids by contacting an amount of biological fluid with a disinfecting or deactivating gas, especially a method for inactivating any viruses or other pathogenic agents present in a biological fluid, typically a bodily liquid, by contacting an amount of the fluid with a gas containing a deactivating component, the method characterized by the steps of:

dividing an amount of the biological fluid into small droplets, contacting the droplets with the gas for a time and in conditions sufficient to inactivate any viruses or agents in the amount of fluid, and collecting the fluid after the contacting step, the size of said droplets being sufficiently small to expose any viruses or pathogenic agents present in the fluid to a deactivating action of said gas.

The method also comprises the step, or steps, of maintaining the droplets in dispersion, or in other words, from preventing the droplets from aggregating, flocculating etc. before their contact with the gas. This step is accomplished preferably by the application of a magnetic and/or electric field upon the space through which said droplets are passed as they are contacted with the gas.

The pathogenic agents are typically viruses, cyanobacteria, bacteria, protozoa and fungi.

The biological fluid may be blood, partial blood, plasma, serum, serum-supplemented medium, semen, milk, whey, trypsin and ascitic fluid.

According to another aspect of the invention, there is provided an apparatus for disinfecting biological fluids by contacting such fluids with disinfecting or deactivating gases, especially an apparatus for inactivating viruses and other pathogenic agents present in bodily fluids, the apparatus comprising:

means for dispersing an amount of said biological fluid into droplets, the size of the droplets being sufficiently small to enable the exposure of substantially all viruses or pathogenic agents present in said amount of said fluid to a deactivating action of said gas, means for contacting said droplets with a gas containing a deactivating component, and means for collecting said droplets after being processed.

Preferably, the apparatus also comprises means for applying electromagnetic fields upon the space through which the droplets are passed as they are contacted with the deactivating gas, e.g. an ozone-containing gas.

BRIEF DESCRIPTION OF THE DRAWINGS

In the drawings in which like numerals represent the same or equivalent elements.

DETAILED DESCRIPTION OF THE PREFERRED EMBODIMENTS OF THE INVENTION

Figure 1:
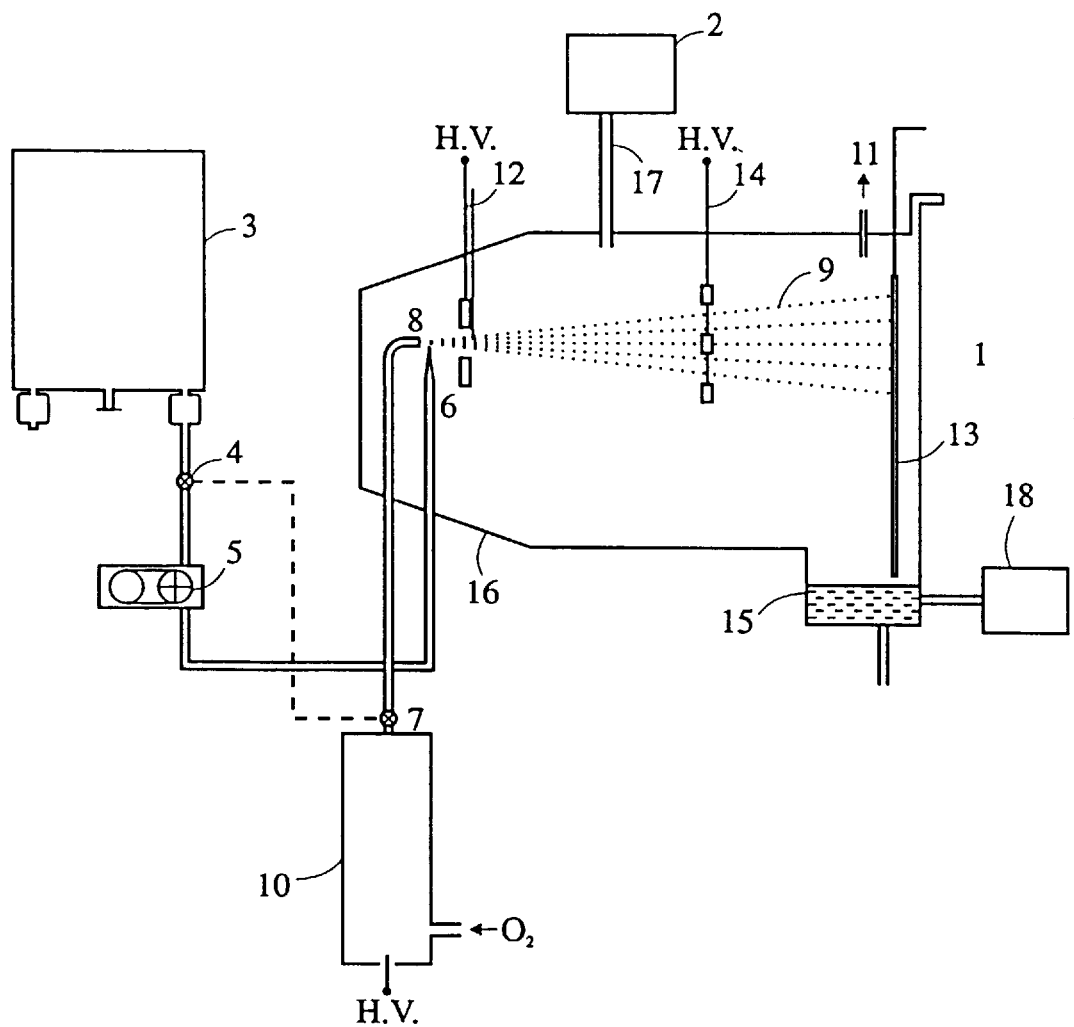
FIG. 1 is a schematic representation of one embodiment of the apparatus of the invention employing the principle of gas blast atomization of liquid through a small orifice.

Nebulization.

In the invention, the fluid is "atomized" into small droplets using a nebulizer. Efforts are made to ensure that there is no cell aggregation or chain formation before sufficient contact of the droplets with the deactivating gas has been attained. The droplets are exposed to a controlled atmosphere containing ozone as the preferred deactivating component. The properties and composition of the fluid affect the effectiveness and efficiency of nebulizing. Hence, the method proposed is fluid-specific, that is, it requires an appropriate nozzle for each given fluid. For example, if one is treating packed red cells, it is advantageous that the droplet be approximately of the same size as a single red blood cell while minimizing red blood cell lysis to less than about 5%. This enables viruses attached to the red blood cell, e.g. budding through the cell membrane, to be exposed to ozone. If the droplets are much larger, the viruses could be sheltered in the spaces between the red cells.

Some droplets may contain only plasma (no cells). Since many viruses are $10^2$ to $10^3$ times smaller than a blood red cell, a cell-free drop could contain many viruses and still be much smaller than a red-cell containing droplet. For these viruses to be inactivated, the gas must diffuse into the liquid rather than react at the surface. In the actual tests conducted to validate the invention, very high inactivation efficiency was attained, as described herein, despite the inevitable presence of some cell-free droplets.

It can be demonstrated that the following factors affect the elimination of the viruses in the droplets: (a) the aerodynamic properties of the droplets; and (b) the absorption of ozone by the droplet in flight. Since the absorption coefficient (the solubility of ozone by liquid at the boundary layer) is governed by Henry's law, the ozone absorption rate is an exponential function of the radius of the droplets. Therefore, the effectiveness of this process will depend on the size of the droplets. In addition, an internal circulation of the fluid within the droplet falling through an ozone atmosphere is caused by shearing at the gas/fluid interface according to Stokes's law.

To achieve the necessary drop (droplet) size distribution, mean drop size, mean drop velocity, spray pattern and concentration of the droplets, the knowledge derived in the experimental aerosol research is useful. The nozzles are characterized in terms of maximum flow rate, available atomizing surface, (horizontal and vertical) orientation and the feed velocity of the liquid. It is expected that the nozzles will resist clogging and will not be prone to over-spray. In the vicinity of the spray, the local conditions (e.g. humidity, temperature) must be considered to appreciate the effects of the evaporation rate and surface tensions on the evolution of the droplets.

Three types of nebulizer systems are considered and discussed herein.

Generally, each system comprises an ozone generator and nebulizer (atomizer), an inactivation chamber, and a droplet collection means.

Compressed Gas Atomizer (or Pressure Jet Atomizer) and Twin Fluid Atomizer.

These devices use aerodynamic forces for atomization. With the compressed gas atomizer, the liquid is injected at high speed into a slow moving or stagnant ambient stream. With the twin fluid atomizer, the liquid is injected at a low speed into a fast moving ambient stream. In both devices, intense shear forces at the interface between the two streams break up the liquid jet. The technique is simple and versatile. The spray characteristics are easily controlled by varying flow parameters.

FIG. 1 illustrates a compressed gas atomizer.

In the inactivation chamber assembly 1, the biological fluid stored in a blood bag 3 passes though an "on-off" valve 4 and peristaltic pump 5 into the nozzle 6 of the compressed gas nebulizer. The "on-off" valve 7 is coupled with valve 4 to control the supply of the $O_3/O_2$ mixture coming from the ozone generator 10 at a pressure of 5 to 30 psi. The ozone generator may contain $O_2$ from $O_3$ separation unit so that a nonreactive gas (e.g. $N_2$, He, etc.) could carry $O_3$/inert-gas mixture to the chamber. The gas is injected through a narrow nozzle 8. The gas jet draws the body fluids out of the nozzle 6 and, due to the confluence of these two jets, the spray 9 is formed between the nozzle 6 and the surface 13 which also serves as an electrode. The system is enclosed in an enclosure 16 made out of a non-wettable plastic, and the processed fluid is collected in the reservoir 15. An additional peristaltic pump 5 can be attached to the reservoir 15 to remove the processed body fluid. The ozone concentration is measured by a conventional ozone monitor 2 which is connected by the tube 17 and the tube 11 vents the used gas mixture to a gas decomposer, not shown. The electrode system 12, 13 and 14 and the redox sensor 18 will be described herein below.

Ultrasonic Nebulizer.

This device establishes a standing wave pattern in the emerging liquid stream the amplitude of which is increased to the point where the wave crests become unstable and collapse. Very fine atomization is achieved at low (1–3 m/s) velocity, making these devices ideal nebulizers with flow rates of 1 to 400 mL/min.

Figure 2:
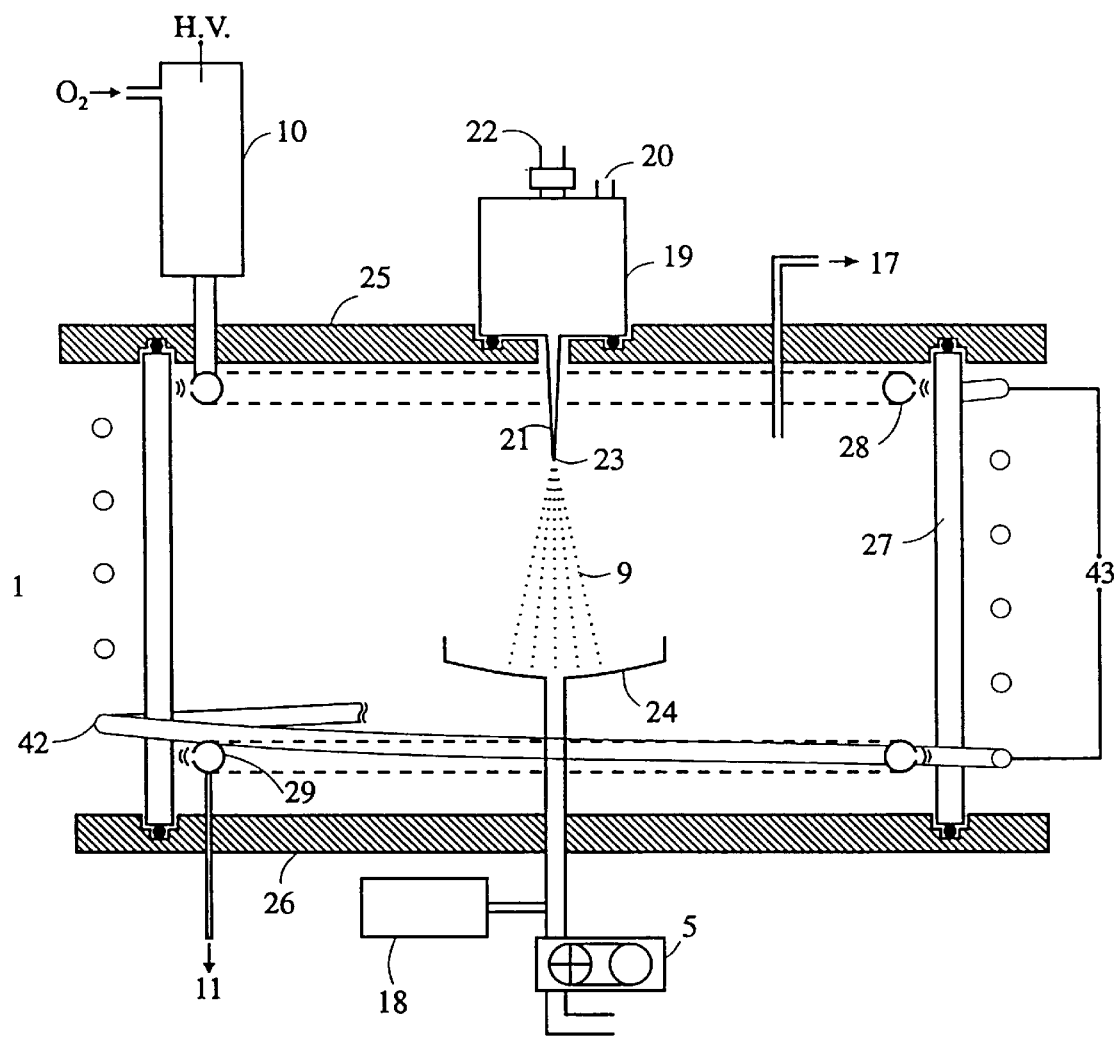
FIG. 2 is a schematic representation of another embodiment, an ultrasonic nebulizer.

The nebulizer system shown in FIG. 2 has a piezoelectric resonant device 19 whose transducer disks are energized by high frequency electrical signals applied to the terminals 20. This results in the propagation of pressure waves in both directions along the nozzle 21. The body liquid inlet is at point 22 and the spray originates at the atomizing surface 23. The droplets are collected at a dish 24. A peristaltic pump 5 removes the liquids from the dish 24. The inactivation chamber is formed between the two stainless-steel flanges 25 and 26 and the glass cylinder 27. Ozone is injected into the chamber via a perforated annulus 28 through twenty-four small-diameter openings therein to ensure that the ozone stream is slow moving. The ozone outlet 29 which is of a similar design as the annulus 28, feeds the used gas to the vent decomposer, not shown, via tube 11.

Rotary Nebulizer.

Figure 3:
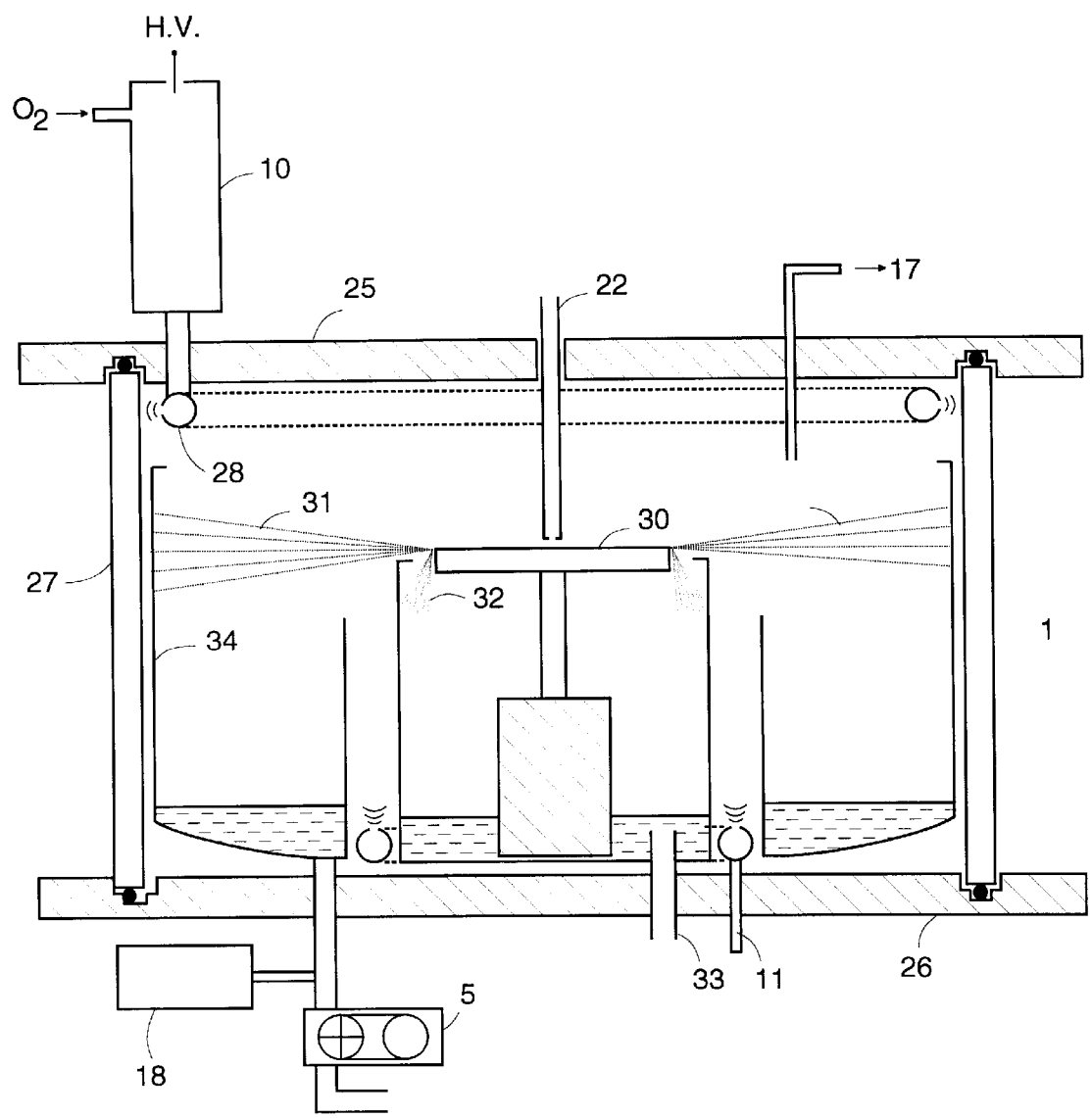
FIG. 3 illustrates schematically a rotary nebulizer system in accordance with the invention.

This device, shown in FIG. 3, uses centrifugal forces for atomization. The liquid supplied by a tube 22 is discharged at high velocity from the edge of a rotating disc 30. Atomization is controlled by the disc speed and liquid flow rate and the droplets have a narrow size range. The droplet size may be reduced by increasing disc speed and by reducing the liquid flow rate. For low-viscosity fluids the performance is greatly enhanced by adding a co-flowing ozone/oxygen stream that separates the droplets into primary (large) and satellite (small) droplets. The primary droplets 31 are substantially mono-dispersive and, during their time of flight from the disc to the collecting non-wettable plastic enclosure 34, they interact with the ozone. The satellite droplets 32 are deflected away by the gas flow and ejected from the system via the exit 33. This type of nebulizer permits an average (500 mL per 15 minutes) flow rate.

Application of Electric and Magnetic fields.

The flight characteristics of the droplets can be augmented and controlled electronically. Each droplet is charged by the electrostatic field produced by a high voltage "ring" electrode 12 placed in front of the nozzle and shown in FIG. 1. This ensures that the droplets do not fuse during the time of flight. The voltage between the "ring" electrode 12 and the ground electrode 13 affects the speed of the droplets and thus controls the virus/ozone interaction (contact) time. To further control the speed of the droplets, another electrode 14 is placed in the space between the ground electrode 13 and the "ring" electrode 12, leading to a classical "triode" structure.

A magnetic field can be applied to increase the flight time of the droplets by making them follow a helical path, due to the magnetic properties of the red cells' haemoglobin. A magnetic field can be produced by a solenoid 42 that is energized by a d.c. source 43. The solenoid is placed in a close proximity of the glass cylinder 27 of FIG. 2. Electromagnetic fields can also be applied correspondingly in the systems shown in FIGS. 1, 3 and 4.

Separation of ozone from oxygen.

When ozone is generated by electrical discharges, a gas mixture ($O_3$—$O_2$ or $O_3$-air) is produced in which the ozone concentration is 1 to 15% by volume. As organic matter is prone to oxidation, it may be important in some applications to minimize the oxidative stress caused by oxygen radicals.

It is feasible to develop a low-temperature distillation (adsorption-desorption) technique. With this technique, it is possible to adsorb ozone on silica-gel (having a low level of elemental Fe impurity) during the adsorption cycle. Subsequently, during a desorption phase (when ozone is separated from oxygen), ozone can be desorbed and carried to the inactivation chamber with an inert gas (e.g., $N_2$, He etc.).

UV radiation.

Figure 4:
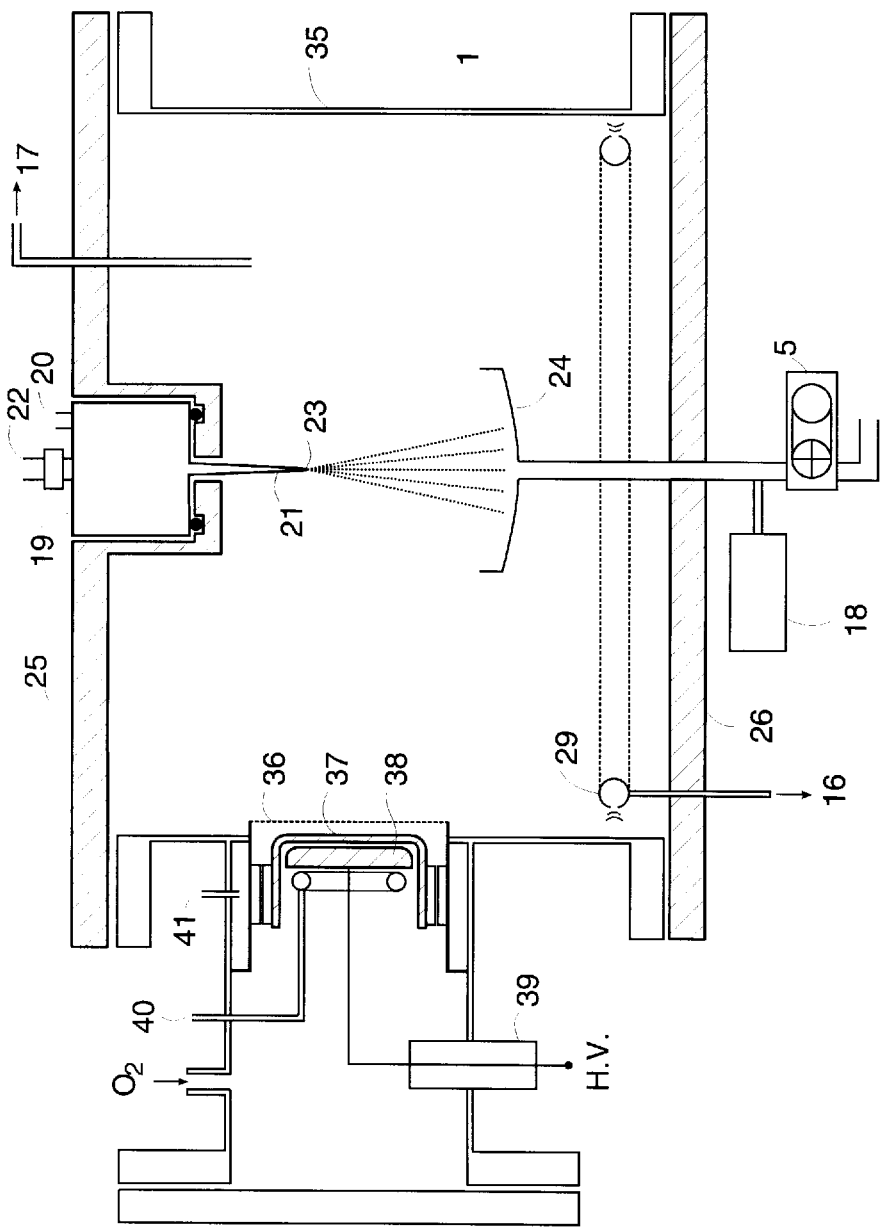
FIG. 4 is a schematic representation of the ultrasonic nebulizer system similar to that of FIG. 2 and additionally employing U.V. radiation to convert oxygen into highly-reactive compounds such as singlet oxygen.

The ozone generator and the inactivation chamber may be integrated into a single unit to generate ozone and to make use of U.V. radiation. As shown in FIG. 4, micro-discharges are produced between a transparent grid 36 and a dielectric 37 (made of aluminium oxides) that is placed over an electrode 38 which is connected to an appropriate H.V. power supply via feed-through 39. The electrodes are cooled by water supplied through connections 40 and 41. The transparent grid permits the transport of U.V radiation into the region where the spray is formed, causing the chemical reaction. To accomplish an uniform ozone production and U.V. irradiation, four ozone generators are used.

The purpose of the above is to cause the biological fluid to react with ozone under the U.V. radiation whereby water of the biological fluid in the spray forms hydrogen peroxide and other highly-reactive cytocidal compounds.

Control of the ozone concentration.

The ozone concentration in the chamber can be measured by taking a gas sample through the tube 17 in FIGS. 1 to 4 and feeding the sample to a conventional ozone monitor 2 operating according to the Beer-Lambert absorption law. It is advisable to measure the ozone concentration in the inactivation chamber and the amount of ozone absorbed in the biological fluid during the treatment. Also, it is recommendable to determine the amount of ozone in the body fluid immediately after the droplets are recombined at the collector plate and stored in the reservoir 15 of FIG. 1 (or the dish 24 of FIG. 2). To achieve this, a conventional redox sensor (not shown) can be modified to detect ozone.

Control of the size of the droplets.

The size distribution of the droplets and their mean velocity can be determined e.g. by means of the Doppler velocity apparatus. This can help optimize the flow rate and the nozzle characteristics of the nebulizer with respect to the droplets' evaporation rate, which is directly proportional to the time of flight. Since the virucidal effectiveness of the system is governed by the product of ozone concentration and the time interval of the flight of droplet, it is possible to determine the longitudinal dimension of the spray by taking into account the velocity of the droplets.

Figure 5:
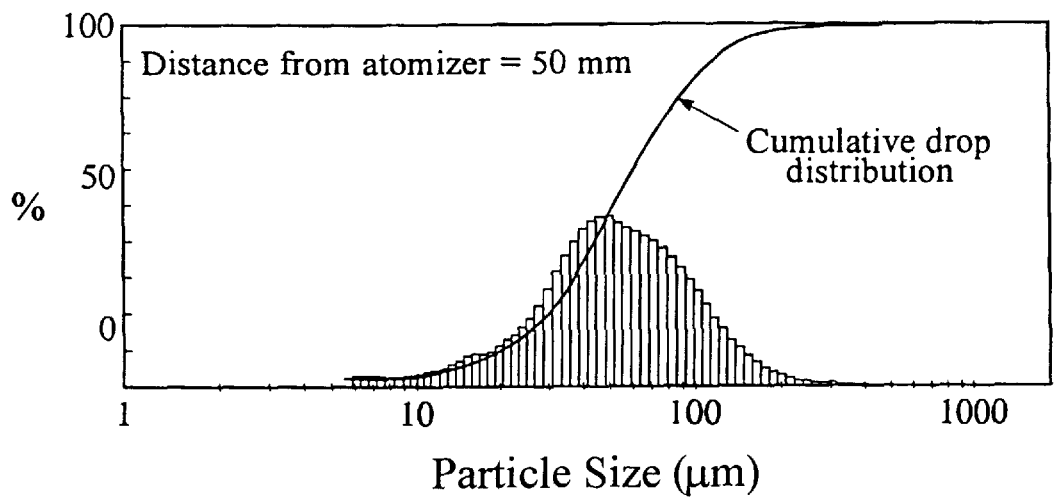
FIG. 5 is a droplet size distribution of the gas blast atomizer of FIG. 1, FIGS. 6a–6e are graphs showing a droplet size distribution of the ultrasonic nebulizer of FIG. 2.
Figures 6A, 6B, 6C, 6D, 6E:
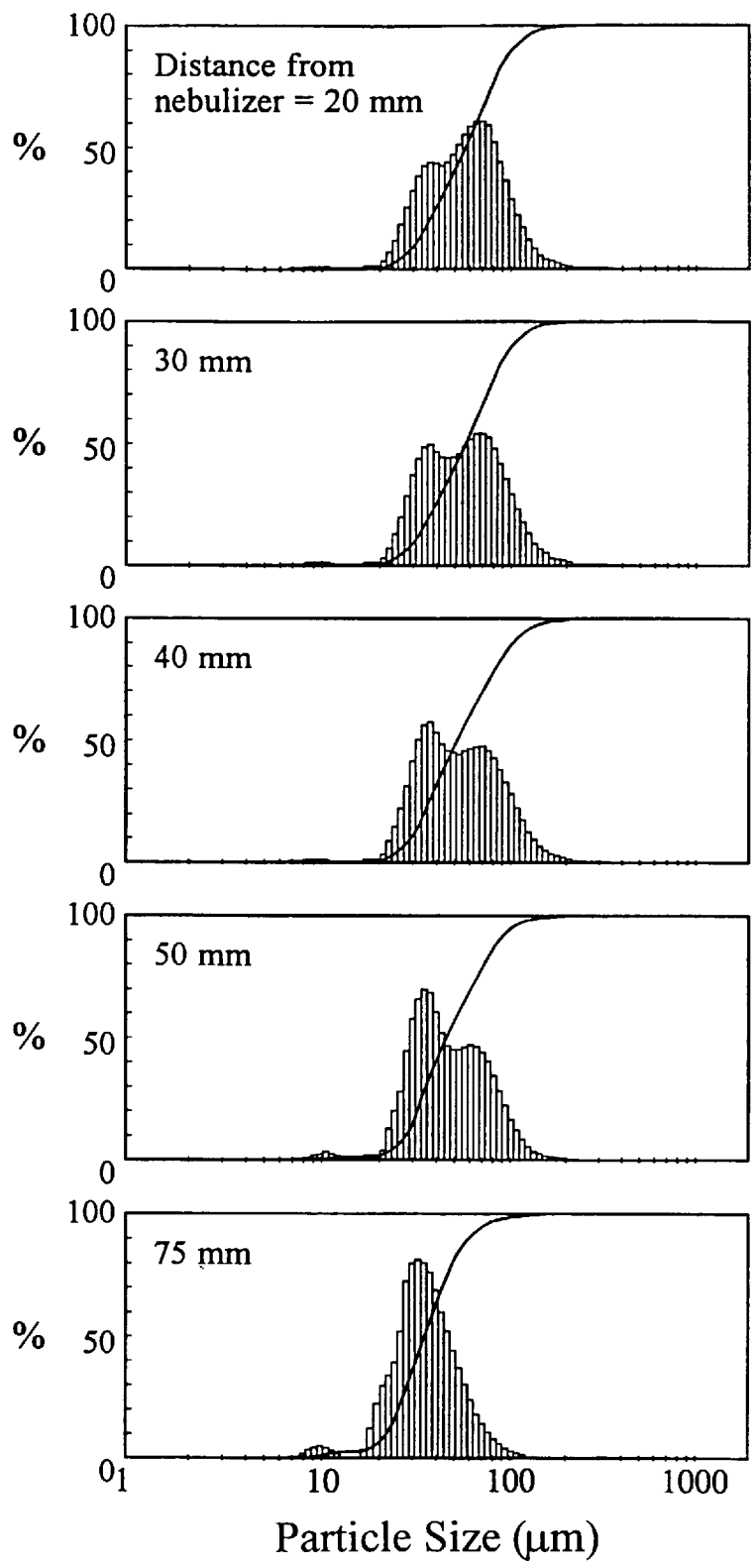

The size distribution of the droplets in the spray, as illustrated in FIGS. 5 and 6 can be described by the Gaussian function (represented by the left side of the equation given below) having mean drop size m and standard deviation $\sigma$. When a virus titer of $2 \times 10^7$ plague forming units (pfu)/ml is added, on average, each droplet of a mean size of 36 $\mu$m contains a single virus. When the droplets are subjected to the ozone atmosphere, the viruses present in the smaller droplets will be the first to be inactivated. The relative number of inactivated viruses is:

$$\frac{1}{\sigma\sqrt{2\pi}} \int_{-\infty}^{x} e^{-\frac{(t-m)^2}{2\sigma^2}} dt = \frac{1}{2}\left(1 + Erf\left(\frac{x-m}{\sigma\sqrt{2}}\right)\right)$$

where Erf is the Error function and from $-\infty$ to $+\infty$, the integral has the value of 1. Therefore, the relative number of viruses surviving the ozone treatment is:

$$s = \frac{1}{2}\left(1 - Erf\left(\frac{x-m}{\sigma\sqrt{2}}\right)\right) \quad (1)$$

Here, x represents a large size droplet (containing a virus) in the distribution that is not affected by the ozone treatment.

Ozone is transferred to the interior of the droplet by diffusion. To simplify the task, experiments were conducted in conditions for a droplet before landing to meet the requirement:

$\pi^2 Dt/R^2 \gg 1$ where R is the radius of the droplet, D is the diffusion constant and t is the time of flight. This implies that the ozone concentration should be uniform throughout the whole volume of the droplets. Hence, the rate of ozone absorption in aqueous solution of the droplets must be compensated by the addition of ozone from outside the sphere. The kinetics of the ozone-liquid interaction can be described as:

$$\frac{dq(t)}{Q_o dt} \approx -\frac{W}{\alpha}$$

in a zero order approximation, where W is the specific rate of gas-liquid feed (liter of gas per liter of suspension) and $\alpha$ is the Henry's law coefficient. The ozone penetrates the surface area of droplets with a diffusion speed v, and in dt will occupy the volume of $4\pi R^2$ v dt. The droplet has the volume of $(4/3)\pi R^3$. If the initial value of $O_3$ is $Q_0$, the total amount of ozone absorbed, q(t) is:

$$q(t) = Q_0\left(1 - e^{\frac{-3vt}{\alpha R}}\right)$$

To inactivate a virus by ozone, we will assume that the dosage must exceed a certain minimum value. When a single virus species is used, q(t) becomes $q_0$=constant. From the above expression, one obtains $$R = -\frac{\beta}{\ln\left(1 - \frac{q_0}{Q_0}\right)} \quad (2)$$

where t becomes $t_0$ (=droplet time of flight) and the parameter $\beta$ is $3vt_0/\alpha$. The ozone concentration, $Q_0$ in the chamber is the only variable. Now, R of Eq. 2 is substituted in Eq. 1 as x=2R, and the theoretical survival curves are produced.

EXAMPLES

To demonstrate some aspects of the proposed concept, a drop of blood was released from a 10 mL syringe with a needle (gauge 14–20) by knocking the needle with a finger. The drops were allowed to free-fall over a distance of 5 to 10 cm until enough blood was collected in a petri dish to do the analysis. The injury (haemolysis) to the red blood cells as indicated by haemolysis was none or minimal (<2%). Using the compressed gas atomizer (FIG. 1) made of glass, we found that 87% of the red blood cells present in the whole blood, had survived the nebulization treatment due to (1) shearing at the tip of the nozzle, (2) the free fall through a gas and (3) the impact on collection. The respective drop size distribution is given in FIG. 5.

To test the virucidal effectiveness of the system, a test material containing blood serum/plasma and a bacterial virus such as the tailless RNA-coliphage MS2 was used. The titre of active test viruses in the plasma sample can be measured easily and accurately by counting the number of plaques which the sample produces on an *Escherichia coli* lawn. The effectiveness of each type is indicated by the level of reduction of the number of plaques that can be produced by the test viruses in treated plasma samples. Coliphage MS2 was used as a model, because it is safe, easy to handle and can grow to high titers in a suitable bacterial host. MS2 is more resistant to chemical disinfections than viruses such as HIV.

Figure 7:
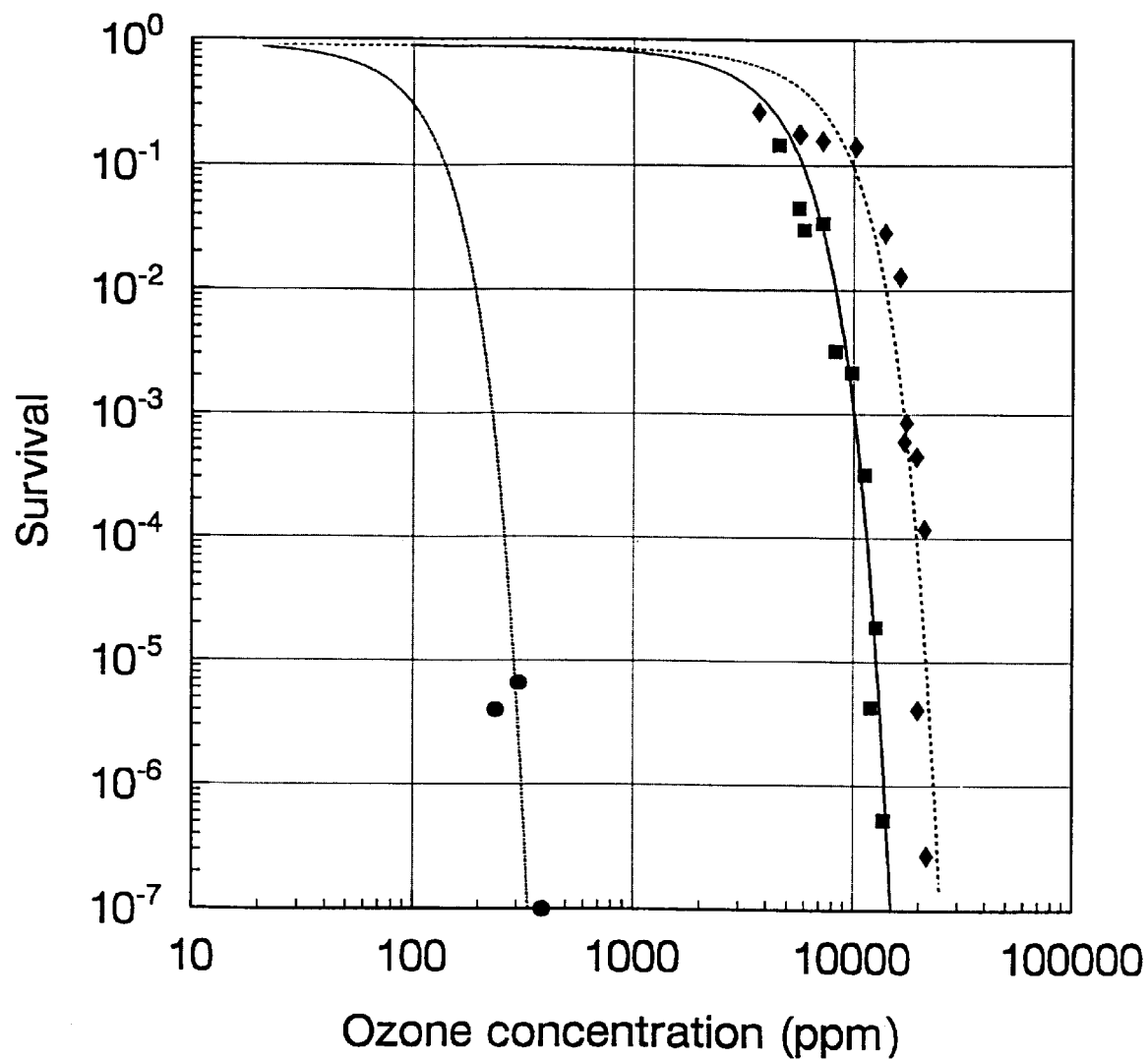
FIG. 7 illustrates survival curves for MS2 vs ozone concentration.

Using the phage MS2 at a concentration of about $2 \times 10^7$ pfu/ml, dose-response curves of MS2 inactivation by ozone were obtained (FIG. 7) with the viruses suspended in (1) Dulbecco's phosphate buffered saline (PBS), (2) a 10% solution of bovine serum in PBS and (3) a 25% bovine serum in PBS. The theoretical curves and experimental points are: on the left (round dots) for PBS, in the middle (squares) for 10% serum and on the right (diamonds) for 25% serum. Data points are the average of three experiments performed in triplicate. Theoretical curves are described by the following expressions for:

saline: $s=0.5(1-\text{Erf}(0.0241(-36.38-5/(\text{Log}(1-(20/Q_0))))))$,

10%: $s=0.5(1-\text{Erf}(0.0241(-36.38-0.11/(\text{Log}(1-(20/Q_0))))))$ and

25%: $s=0.5(1-\text{Erf}(0.0241(-36.38-0.065/(\text{Log}(1-(20/Q_0))))))$.

The ultrasonic nebulizer shown in FIG. 2 was used in the actual experiments, wherein, as determined using a Doppler velocity equipment, m was 36.38 $\mu$m and $\sigma$ was 29.38 $\mu$m$^{-1}$ at a distance of 65 mm from the tip of the nozzle. The flow rate was 18 ml/minute. The nozzle 21 (FIG. 2) was kept at ground potential and the dish 24 was held at the potential of 12 kV giving the average (d.c.) field of about 200 V/cm. Magnetic field was not applied. Ozone concentration varied from 20 to $2*10^4$ ppm, and the time of flight of the droplets was about 1 sec.

A comparison of the experimental points and the theoretical curves for MS2 (FIG. 7) shows that the curves and points form a semi-sigmoid of congruent data. The addition of calf serum concentration to a phosphate buffered saline (PBS) only results in moving the curve to the right. The theoretical curves were computed using Eqs. 1 and 2 for m and $\sigma$ given above. It was assumed that $q_0$ has the value of 20 ppm. To obtain a good fit to the experimental points, a set of value for $\beta$ was attempted. It was found that $\beta$ has the value of 5, 0.11 and 0.065 for PBS, a 10% serum and a 25% serum, respectively. The values for $\beta$ are given when $\ln(x)$ is converted to $\log(x)=\log_{10}(x)$. As MS2 is more resistant to chemical disinfections than HIV, these results indicate a good possibility to kill viruses such as the hepatitis viruses, parvoviruses and HIV's. It is shown by Carpendale and Freeberg, supra, that ozone inactivates HIV at noncytotic concentrations (without affecting blood components).

The analysis given above could be expanded to account for the interaction of ozone with a virus suspension in the shape of a thin film and the experimental findings of prior art (Bolton et al thin film technique) would thereby be better appreciated. If this is done (e.g. by re-plotting their results on the log-log scale, and by adopting the theory for their thin film case), we find again a semi-sigmoid of congruent data, describing the ozone inactivation of the influenza A virus (WSN strain) and the *vesicular stomatitis* virus vs time. For example, Bolton et al, supra, observed that exposure of *vesicular stomatitis* virus to 0.64 ppm of ozone for 16 hours caused 5 $\log_{10}$ reduction in the virus viability.

The present invention was also examined for its viability to inactivate the spores of the bacterium *Bacillus subtilis*. Such spores are routinely used to assess the sporicidal activity of liquid and gaseous chemicals and as biological indicators to validate the performance of stream and gas sterilizers. The bacterium was grown in Columbia Broth (Difco, Detroit, Mich.) diluted 10-fold in deionized water. In this medium, there was nearly a 100% sporulation after 48 hours at 37° C. The spores were washed three times in deionized water and suspended in the test medium to a final concentration of $10^8$ pfu/ml.

When *B. subtilis* spores were suspended in PBS and nebulized in the presence of ozone, there was >5 $\log_{10}$ reduction in their viability.

The present invention and discoveries made within its scope offer many opportunities of minimizing the ozone concentration required to kill viruses. If a given volume of fluid is divided into n spheres of equal size, the radius of the droplets is decreased by a factor equal to the cube root of n. This factor enters the exponential relationship in the kinetics of the ozone-liquid interaction ($q(t) \sim \exp(-W/\alpha)$). Therefore, it is necessary to decrease the droplets size as much as possible in order that the virus inactivation is done at smaller ozone concentration. However, if a very small droplet size is chosen, the use of hydro-cyclone technology to collect droplets may become necessary.

The details of the method and apparatus for the inactivation of viruses in body fluids by $O_3$ technology described herein, as well as the variations suggested thereof, are only illustrative and are not intended to limit the spirit or scope of the invention set forth in the appended claims.

I claim:

1. A method of disinfecting a biological fluid containing viruses or pathogenic agents by interaction with a gas containing a disinfecting component, the method characterized by the steps of dividing an amount of said fluid into small droplets, contacting said droplets with said gas for a time and in conditions sufficient to inactivate said viruses or agents in said amount of fluid, and collecting said fluid after the contacting step, the size of said droplets being sufficiently small to expose any viruses or pathogenic agents present in said fluid to a deactivating action of said gas.

2. The method of claim 1 wherein said droplets are passed through an atmosphere of said gas, the method comprising the step of maintaining said droplets in a dispersed condition during their contact with said gas.

3. The method of claim 2 wherein said step is accomplished by the application of an electromagnetic field upon a space through which said droplets are passed during their contact with said gas.

4. The method of claim 1 wherein said pathogenic agents are selected from the group consisting of viruses, cyanobacteria, bacteria, protozoa and fungi.

5. The method of claim 1 wherein said biological fluid is selected from the group consisting of blood, partial blood, plasma, serum, serum-supplemented media, semen, milk, whey, trypsin, and ascitic fluid.

6. The method of claim 3 wherein said droplets are electrostatically charged during their contact with said gas.

7. The method of claim 1 wherein said biological liquid has magnetic properties, the method further comprising the step of applying a magnetic field onto a space in which said droplets are contacted with said gas.

8. An apparatus for disinfecting biological fluids by contacting such fluids with a disinfecting or deactivating gas, said apparatus comprising:

dispersing means for dispersing an amount of said biological fluid into droplets, the size of the droplets being sufficiently small to enable the exposure of substantially all viruses or agents present in said amount of said fluid to a deactivating action of said gas, means for contacting said droplets with a gas containing a deactivating component, and means for collecting said droplets after being processed.

9. The apparatus of claim 8, further comprising means for maintaining said droplets in a dispersed condition during their contact with said gas.

10. The apparatus of claim 9 wherein said dispersion-maintaining means are means for applying electromagnetic fields upon the space through which the droplets are passed as they are contacted with the deactivating gas.

11. The apparatus of claim 8 wherein said dispersing means are ultrasonic nebulizing means.

12. The apparatus of claim 8 wherein said dispersing means are compressed gas nebulizing means.

13. The apparatus of claim 8 wherein said dispersing means are rotary nebulizing means.

14. The apparatus of claim 8 further comprising ultraviolet radiation means for irradiating the biological fluid.

15. An apparatus for disinfecting biological fluids by contacting such fluids with an ozone-containing gas, said apparatus comprising an ozone generating means a nebulizing means for dispersing a biological fluid into small droplets, contacting means for passing said droplets through an atmosphere of said gas to achieve a contact of said droplets with said gas, collecting means for collecting said droplets after said contact.

16. The apparatus of claim 15 further comprising anti-aggregation means for preventing said droplets from aggregation or agglomeration during the time of flight of said droplets.

17. The apparatus of claim 16 wherein said anti-aggregation means are triode means.

18. The apparatus of claim 15 wherein said contacting means comprise a contacting chamber.

19. The apparatus according to claim 18 wherein said ozone generating means is integral with said contacting chamber.

20. The apparatus of claim 18 further comprising means for applying a magnetic field across said contacting chamber.

* * * * *